(12) United States Patent
Semler et al.

(10) Patent No.: US 9,050,140 B2
(45) Date of Patent: Jun. 9, 2015

(54) APPARATUS FOR STABILIZING VERTEBRAL BODIES

(71) Applicant: Blackstone Medical, Inc., Lewisville, TX (US)

(72) Inventors: Mark Evald Semler, McKinney, TX (US); Francesco Alfredo Larosa, Neptune, NJ (US)

(73) Assignee: BLACKSTONE MEDICAL, INC., Lewisville, TX (US)

( * ) Notice: Subject to any disclaimer, the term of this patent is extended or adjusted under 35 U.S.C. 154(b) by 0 days.

(21) Appl. No.: 13/651,640

(22) Filed: Oct. 15, 2012

(65) Prior Publication Data

US 2013/0041409 A1 Feb. 14, 2013

Related U.S. Application Data

(63) Continuation of application No. 12/190,423, filed on Aug. 12, 2008, now Pat. No. 8,287,571.

(51) Int. Cl.
*A61B 17/70* (2006.01)
(52) U.S. Cl.
CPC ......... *A61B 17/7004* (2013.01); *A61B 17/7023* (2013.01); *A61B 17/7025* (2013.01); *A61B 17/7031* (2013.01)
(58) Field of Classification Search
CPC ........... A61B 17/7004; A61B 17/7023; A61B 17/7025; A61B 17/7031
USPC ................................................. 606/254–262
See application file for complete search history.

(56) References Cited

U.S. PATENT DOCUMENTS

| 4,743,260 | A | 5/1988 | Burton |
| 5,034,011 | A | 7/1991 | Howland |

(Continued)

FOREIGN PATENT DOCUMENTS

| FR | 2730918 A1 | 8/1996 |
| FR | 2814936 A1 | 4/2002 |

(Continued)

OTHER PUBLICATIONS

International Search Report and Written Opinion, PCT/US2009/053600, dated Sep. 29, 2009, 8 pages.

(Continued)

*Primary Examiner* — Jan Christopher Merene
*Assistant Examiner* — Atiya Mahmud
(74) *Attorney, Agent, or Firm* — Baker & McKenzie LLP

(57) ABSTRACT

A dynamic stabilization apparatus comprises elongated members mounted within the proximal end of anchoring devices that are placed in adjacent vertebral bodies. A flexible element having elastic properties within the applicable range of loading, for example loads that the spine experiences, is disposed between the proximal ends of the elongated members. At least one additional flexible element is mounted about the proximal ends of the elongated members adjacent the central flexible element. A housing encapsulates the proximal ends of the members such that the flexible element and the additional flexible elements are contained therein. As compressive, tensile, angular, shear and rotational forces are applied to the elongated members the central flexible element and the additional flexible elements interact with the elongated members and the housing to allow for motion of the elongated members.

11 Claims, 18 Drawing Sheets

(56) References Cited

U.S. PATENT DOCUMENTS

| | | |
|---|---|---|
| 5,092,866 A | 3/1992 | Breard |
| 5,180,393 A | 1/1993 | Commarmond |
| 5,242,446 A | 9/1993 | Steffee |
| 5,282,863 A | 2/1994 | Burton |
| 5,375,823 A | 12/1994 | Navas |
| 5,415,661 A | 5/1995 | Holmes |
| 5,480,401 A | 1/1996 | Navas |
| 5,480,442 A | 1/1996 | Bertagnoli |
| 5,507,816 A | 4/1996 | Bullivant |
| 5,540,688 A | 7/1996 | Navas |
| 5,562,737 A | 10/1996 | Graf |
| 5,672,175 A | 9/1997 | Martin |
| 5,961,516 A | 10/1999 | Graf |
| 6,241,730 B1 | 6/2001 | Alby |
| 6,267,764 B1 | 7/2001 | Elberg |
| 6,293,949 B1 | 9/2001 | Justis |
| 6,443,437 B1 | 9/2002 | Beyene et al. |
| 6,761,719 B2 | 7/2004 | Justis |
| 6,986,771 B2 | 1/2006 | Paul |
| 7,029,475 B2 | 4/2006 | Panjabi |
| 7,083,621 B2 | 8/2006 | Shaolian et al. |
| 7,125,410 B2 | 10/2006 | Freudiger |
| 7,282,065 B2 | 10/2007 | Kirschman |
| 7,291,150 B2 | 11/2007 | Graf |
| 7,294,129 B2 | 11/2007 | Hawkins et al. |
| 7,326,210 B2 | 2/2008 | Jahng et al. |
| 7,326,250 B2 | 2/2008 | Beaurain et al. |
| 7,338,527 B2 | 3/2008 | Blatt et al. |
| 7,361,196 B2 | 4/2008 | Fallin et al. |
| 7,597,027 B2 | 10/2009 | Kwon |
| 7,763,048 B2 | 7/2010 | Fortin et al. |
| 7,776,071 B2 | 8/2010 | Fortin et al. |
| 2004/0002708 A1 | 1/2004 | Ritland |
| 2004/0049189 A1 | 3/2004 | Le Couedic et al. |
| 2004/0243127 A1 | 12/2004 | Vincent-Prestigiacomo |
| 2005/0056979 A1 | 3/2005 | Studer |
| 2005/0065514 A1 | 3/2005 | Studer |
| 2005/0096659 A1 | 5/2005 | Freudiger |
| 2005/0131407 A1 | 6/2005 | Sicvol et al. |
| 2005/0165396 A1 | 7/2005 | Fortin et al. |
| 2005/0171540 A1 | 8/2005 | Lim et al. |
| 2005/0171543 A1 | 8/2005 | Timm et al. |
| 2005/0182401 A1 | 8/2005 | Timm et al. |
| 2005/0261685 A1 | 11/2005 | Fortin et al. |
| 2005/0277922 A1 | 12/2005 | Trieu et al. |
| 2006/0036240 A1 | 2/2006 | Colleran et al. |
| 2006/0084984 A1* | 4/2006 | Kim .................... 606/61 |
| 2006/0084991 A1 | 4/2006 | Borgstrom et al. |
| 2006/0142760 A1 | 6/2006 | McDonnell |
| 2006/0149238 A1 | 7/2006 | Sherman et al. |
| 2006/0189984 A1 | 8/2006 | Fallin et al. |
| 2006/0212033 A1 | 9/2006 | Rothman et al. |
| 2006/0229609 A1 | 10/2006 | Wang |
| 2006/0247637 A1 | 11/2006 | Colleran |
| 2006/0264935 A1 | 11/2006 | White |
| 2006/0264940 A1 | 11/2006 | Hartmann |
| 2007/0016190 A1 | 1/2007 | Martinez |
| 2007/0016193 A1 | 1/2007 | Ritland |
| 2007/0016201 A1 | 1/2007 | Freudiger |
| 2007/0049936 A1 | 3/2007 | Colleran et al. |
| 2007/0055244 A1 | 3/2007 | Jackson |
| 2007/0093813 A1 | 4/2007 | Callahan, II et al. |
| 2007/0100341 A1 | 5/2007 | Reglos et al. |
| 2007/0118122 A1* | 5/2007 | Butler et al. .................... 606/61 |
| 2007/0123866 A1 | 5/2007 | Gerbec et al. |
| 2007/0135815 A1 | 6/2007 | Gerbec et al. |
| 2007/0191832 A1 | 8/2007 | Trieu |
| 2007/0191846 A1 | 8/2007 | Bruneau et al. |
| 2007/0225710 A1 | 9/2007 | Jahng et al. |
| 2007/0270814 A1 | 11/2007 | Lim et al. |
| 2007/0270821 A1 | 11/2007 | Trieu et al. |
| 2007/0270860 A1 | 11/2007 | Jackson |
| 2007/0276380 A1 | 11/2007 | Jahng et al. |
| 2007/0288008 A1 | 12/2007 | Park |
| 2007/0288011 A1 | 12/2007 | Logan |
| 2008/0033435 A1 | 2/2008 | Studer et al. |
| 2008/0058812 A1* | 3/2008 | Zehnder .................... 606/61 |
| 2008/0065078 A1 | 3/2008 | Graf |
| 2008/0097441 A1 | 4/2008 | Hayes et al. |
| 2008/0125777 A1 | 5/2008 | Veldman et al. |
| 2008/0125787 A1 | 5/2008 | Doubler et al. |
| 2008/0140076 A1 | 6/2008 | Jackson |
| 2008/0147122 A1 | 6/2008 | Jackson |
| 2008/0172091 A1 | 7/2008 | Anderson |
| 2008/0177318 A1 | 7/2008 | Veldman et al. |
| 2008/0183213 A1 | 7/2008 | Veldman et al. |
| 2008/0195208 A1 | 8/2008 | Castellvi et al. |
| 2009/0048631 A1 | 2/2009 | Bhatnagar et al. |
| 2009/0099608 A1 | 4/2009 | Szczesny |
| 2009/0234388 A1 | 9/2009 | Patterson et al. |
| 2009/0326583 A1 | 12/2009 | Moumene et al. |
| 2010/0069964 A1 | 3/2010 | Lechmann |

FOREIGN PATENT DOCUMENTS

| | | |
|---|---|---|
| JP | 7-289562 | 7/1995 |
| JP | 2005-504566 A | 2/2005 |
| JP | 2008-502448 A | 1/2008 |
| WO | 2007/103404 A2 | 9/2007 |

OTHER PUBLICATIONS

Japanese Office Action, Application No. 2011-523147, dated Aug. 13, 2013, 6 pages.

Japanese Office Action, JP Application No. 2011-523147, dated Dec. 10, 2013, 4 pages.

Extended European Search Report, Application No. 09807249.9-1506/2320814 PCT/US2009/053600, dated Oct. 7, 2013, 8 pages.

* cited by examiner

APPARATUS FOR STABILIZING VERTEBRAL BODIES

CROSS-REFERENCE TO RELATED APPLICATIONS

This is a continuation application of U.S. application Ser. No. 12/190,423, which was filed on Aug. 12, 2008 and which is incorporated herein by reference in its entirety.

TECHNICAL FIELD

The present invention relates to stabilization of the vertebrae of the spinal column and, more particularly, to an apparatus whereby securing members are implanted and fixed into a portion of a patient's spinal column and a longitudinal member including flexible, semi-rigid rod-like structures of various cross-sections (hereinafter referred to as "rods") are connected and fixed to the upper ends of the securing members to provide stabilization of the spinal column.

BACKGROUND

Degenerative spinal column diseases, for example, disc degenerative diseases (DDD), spinal stenosis, and spondylolisthesis can be corrected by surgical procedures. Typically, spinal decompression is the first surgical procedure that is performed and results in the reduction of pressure in the spinal canal and on nerve roots located therein. Spinal decompression seeks to remove tissue that is applying pressure to the nerve bundle and thus relieve pain. This can result, however, in weakening the spinal column.

Certain surgical procedures, for example posterolateral fusion whereby adjacent vertebral bodies are fused together is often necessary to restore spinal stability following the decompression procedure. Fusion of adjacent vertebral bodies requires that the bone grow together and employs a bone graft or other biological growth agent. In order to maintain the grafting material in place and preserve stability during bone growth, a spinal fixation device is typically used to support the spinal column until a desired level of fusion is achieved. Depending on a patient's particular circumstances and condition, a spinal fixation surgery can sometimes be performed immediately following decompression, without performing the fusion procedure. The fixation surgery is performed in most cases because it provides immediate postoperative stability and, if fusion surgery has also been performed, it provides support of the spine until sufficient fusion and stability has been achieved.

Conventional methods of spinal fixation utilize a rigid spinal fixation device to support and prevent movement of an injured spinal part. These conventional spinal fixation devices include: fixing screws configured to be inserted into the spinal pedicle or sacrum to a predetermined depth and angle, rods or plates configured to be positioned adjacent to the injured spinal part, and coupling elements for connecting and coupling the rods or plates to the fixing screws such that the injured portion of the spin is supported and held in a relatively fixed position by the rods or plates. The connection units prevent further pain and injury to the patient by substantially restraining the movement of the spinal column.

Because the connection units prevent normal movement of the spinal column, after prolonged use, the spinal fixation device can cause ill effects, such as adjacent level syndrome (transitional syndrome) or fusion disease that result in further complications and abnormalities associated with the spinal column. The high rigidity of the rods or plates used in conventional fixation devices causes these disorders due to the patient's joints being fixated by the nature of surgery. The movement of the spinal joints located above or under the operated area is increased. Consequently, such spinal fixation devices cause decreased mobility of the patient and increased stress and instability to the spinal column joints adjacent to the operated area.

It has been reported that excessive rigid spinal fixation is not helpful to the fusion process due to load shielding. As an alternative, semi-rigid spinal fixation devices have been utilized to address this problem while assisting the bone fusion process. For example, U.S. Pat. No. 5,375,823—Navas and U.S. Pat. No. 6,241,730—Alby each disclose a piston configuration mounted between fixing screws having a flexible material or spring element enclosed within a sleeve allowing for axial dampening. Although providing for a greater range of motion than a fixed rod, these devices fail to accommodate for a full range of physiological motion, for example axial torsion or twisting, and are not well-suited for spinal stabilization absent fusion. Thus, in the end these devices do not fully prevent the problem of rigid fixation resulting from fusion.

To solve the above-described problems associated with rigid fixation, semi-rigid and generally flexible devices have been developed. U.S. Publication No. 2006/0264940—Hartmann discloses a flexible spring element connected to a rod and an axially opposed hollow body. The spring element and hollow body have corresponding bores that receive a clamping element. The clamping element has a convex face that abuts the end wall of the internal bore of the spring element during deformation of the spring element under axial loading of the device. The shape of the end of the clamping element controls the spring characteristics of element. While this device functions to provide a greater range of motion during compression it relies upon the spring element as a load bearing structure in tension. This is not an optimal design to handle the long-term cyclical loading the device will experience when implanted.

U.S. Pat. No. 5,672,175—Martin discloses a flexible spinal fixation device which utilizes a flexible rod made of metal alloy and/or a composite material. Additionally, compression or extension springs are coiled around the rod for the purpose of providing de-rotation forces on the vertebrae in a desired direction. However, this approach is primarily concerned with providing a spinal fixation device that permits "relative longitudinal translational sliding movement along [the] vertical axis" of the spine and has a solid construction with a relatively small diameter in order to provide a desired level of flexibility. Because they are typically very thin to provide suitable flexibility, such a rod is prone to mechanical failure and have been known to break after implantation in patients. Similarly, U.S. Publication No. 2007/0270814—Lim shows a vertebral stabilizer that has mobility during compression, extension and rotation. A connecting member such as flexible rods, cables or braided steel are anchored at their distal and proximal ends to engaging portions and are coaxially located within a flexible member. While the connecting members can bend to accommodate shear when the spine is twisted this device has been shown to fail due to fatigue once implanted.

There is no spinal fixation device that can provide for a full range of physiological motion when implanted in a patient. In addition, few devices that attempt to accommodate a range of physiological motion can withstand long-term loading conditions. Therefore, there is a need for an improved dynamic spinal fixation device.

SUMMARY

Elongated members such as rods, plates and the like are often mounted to span vertebral bodies in order to provide stability to localized regions of the spine. These devices are typically mounted to the vertebral bodies via an anchoring device such as a member having threads at its distal end, allowing for attachment to the spine and a proximal end that accepts the elongated member. For example, at least two threaded members are placed in adjacent vertebral bodies and the elongated members are mounted to the proximal end of threaded members so as to span the vertebral bodies. Rigid elongated bodies are typically employed in order to prevent motion between the vertebral bodies.

According to the invention, a dynamic stabilization apparatus is provided. The apparatus comprises elongated members such as rods mounted within a housing. The elongated members are mounted within the proximal end of anchoring devices that are placed in adjacent vertebral bodies. A central flexible element having elastic properties within the applicable range of loading, for example loads that the spine experiences, is disposed between the proximal ends of the elongated members. At least one additional flexible element is mounted about the proximal ends of the elongated members adjacent the central flexible element. The housing encapsulates the proximal ends of the members such that the central flexible element and the additional flexible elements are contained therein. As compressive, tensile, angular, shear and rotational forces are applied to the elongated members the central flexible element and the additional flexible elements interact with the elongated members and the housing to allow for motion of the elongated members. The degree of permissible motion may be varied, for example, by varying the material from which the flexible members are constructed.

The housing may be generally cylindrical and has openings at each end for receiving the elongated members there through. In one embodiment of the invention, the housing is constructed from a generally rigid material that will not deform under the physiological loading encountered within the spine. The housing may be formed from a first and a second casing wherein each of the casings have an opening therein. The casings include an engagement feature such that after the elongated members are inserted through the openings the casings are engaged together to assemble the apparatus.

In one embodiment of the invention the proximal ends of the elongated elements are larger than the central and distal portions of the elongated member. For example, one or both of the proximal ends are flanges. The flange includes an inward surface facing the central flexible element and an outward surface facing the distal end of said elongated member. The inward surface may be generally concave and contacts an outer facing surface of the central flexible element that is convex. Alternatively, the inner surface of the flange may be convex while the contacting or outer surface of the central flexible element is concave. A variety of shapes for the two surfaces may be employed including having both surfaces be flat.

The central flexible member may be constructed from a polymer and has a first and a second outward facing surface. The central flexible member resists rotational and compressive forces. The inward surface of each of the flanges contacts the outer facing surfaces of the central flexible element. Protrusions located on either the outward surface of the central element or the inward surface of the flanges engages with corresponding recesses to form an anti-torsional coupling. As the elongated members are rotated about their axis in opposite directions the engagement of the protrusions within the recesses causes the central flexible element to elastically deform, resisting the motion. In addition, as the elongated members experience a compressive force the flanges engage the central flexible element. The central flexible element is compressed resisting while allowing motion of the elongate members. Eventually the central flexible element deforms such that it contacts the housing further increasing the resistance to the motion of the elongated members.

The outward surface of the proximal end of the elongate members or the flange contacts a surface of the additional flexible element. A variety of shapes can be employed for the outward surface of the flange and the corresponding contacted surface of the additional flexible element. The shaping of these surfaces may be varied in order to create a desired dynamic response. As with the central element, the additional flexible elements may be constructed from a polymer. The additional flexible elements serve as an axial and radial buffer between the housing and the elongated members. For example, as the elongated members are subjected to an axial or radial force, the flange pushes on and deforms the additional flexible member which resists the motion of the elongated members. Varying the elastic properties of the central and flexible members allows the load-displacement response of the apparatus to be customized.

BRIEF DESCRIPTION OF THE DRAWINGS

The features and advantages of the invention will be apparent to those of ordinary skill in the art from the following detailed description of which.

DETAILED DESCRIPTION OF ILLUSTRATIVE EMBODIMENTS

Figure 1:
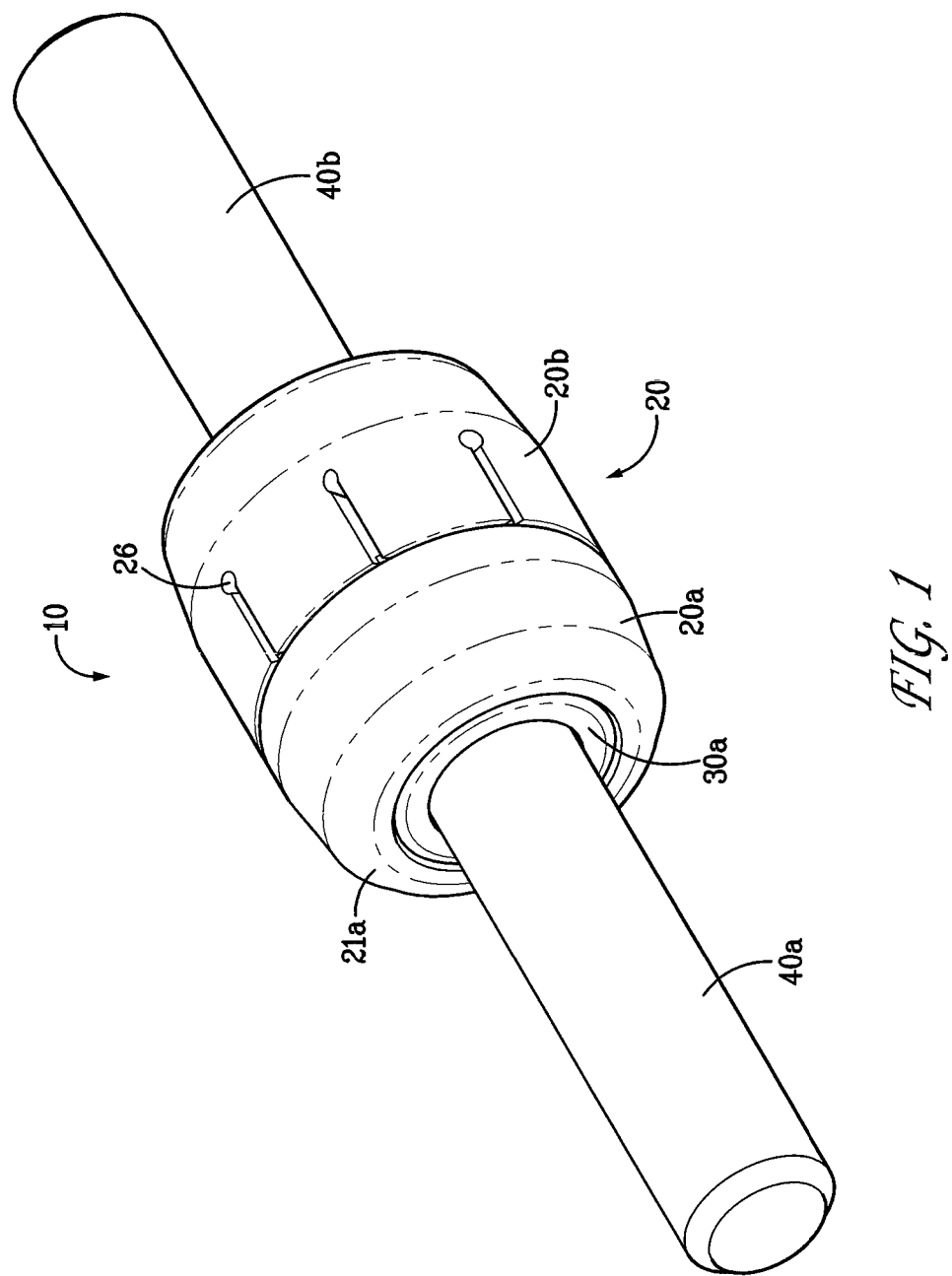
FIG. 1 is an isometric view of to an embodiment of the present invention.

An implantable dynamic apparatus for stabilizing a desired region of the spine will be described with reference to FIGS. 1-18. As shown in FIGS. 1-4 the apparatus 10 of the present invention generally comprises elongated members 40a, b mounted within a housing 20. A central element 50 having elastic properties is disposed between the proximal ends of the two elongated members 40a, b. At least one additional flexible or compressible element 30a, b is mounted about the proximal end of the elongated members 40a, b adjacent the central element 50. The housing 20 encapsulates the proximal ends of the elongated members 40a, b such that the central element 50 and the at least one additional flexible or compressible element(s) 30a, b are contained therein.

The elongated members 40a, b may be constructed from materials having sufficient strength and rigidity to resist fracture and plastic deformation under the loads experienced by the spine. Materials such as titanium, titanium alloy, stainless steel or a polymer such as PEEK or carbon fiber may be employed. The elongated members 40a, b may have a variety of shapes such as cylindrical or polygonal and need not both have the same shape. The construction of the components of the apparatus 10 may be varied to meet the particular conditions of the patient in which the apparatus 10 will be utilized. For example, the material used to construct the central element 50 may be varied or the size and shape or the elongated members 40a, b can be varied such that each member has a different shape or is constructed from a different material.

Figure 12:
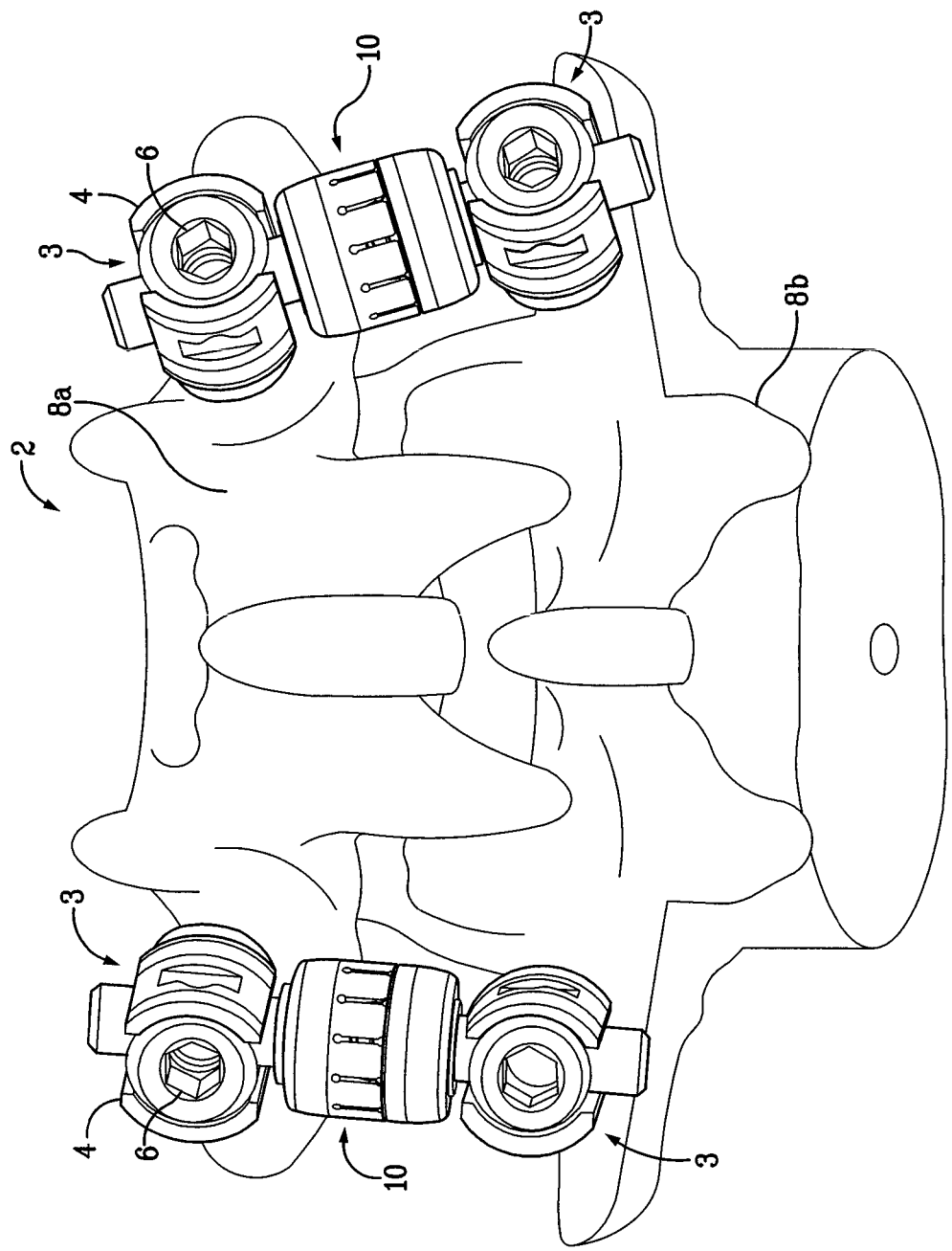
FIG. 12 is a posterior view showing an embodiment of the present invention placed on a section of the spine.

As shown in FIG. 12, one or more of apparatus 10 can be mounted between adjacent vertebral bodies 8a, b in order to provide stability to localized regions of the spine 2. Typically, stabilization devices such as apparatus 10 are mounted to the vertebral bodies 8a, b via an anchoring device 3. The device may comprise a member having threads at its distal end, not shown in the drawings that allow for attachment to the honey tissue of the spine and a proximal end 4 that accepts the distal ends of elongated members 40a, b. Alternatively, the distal end may comprise a clamp or other gripping surface. A retaining member 6 locks the distal ends of the elongated members 40a, b to the anchoring devices 3. As will be described in greater detail below, when the spine experiences the normal range of physiological motion the central element 50 and the additional flexible or compressible elements 30a, b interact with the elongated members 40a, b and the housing 20 to stabilize the spine while allowing for controlled movement of the adjacent vertebral bodies 8a, b.

Figure 2:
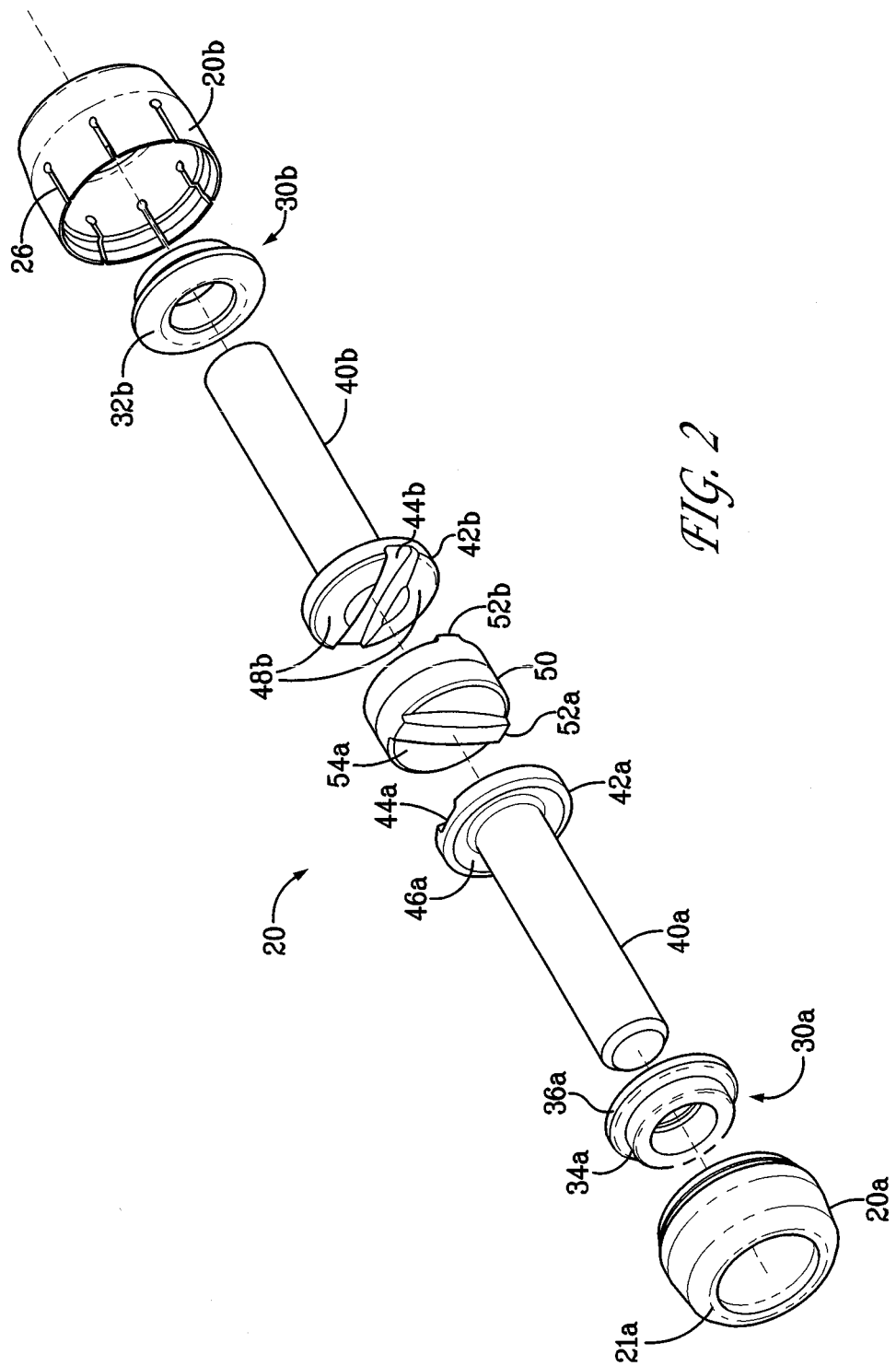
FIG. 2 is an exploded view of the components of an embodiment of the present invention.
Figure 3:
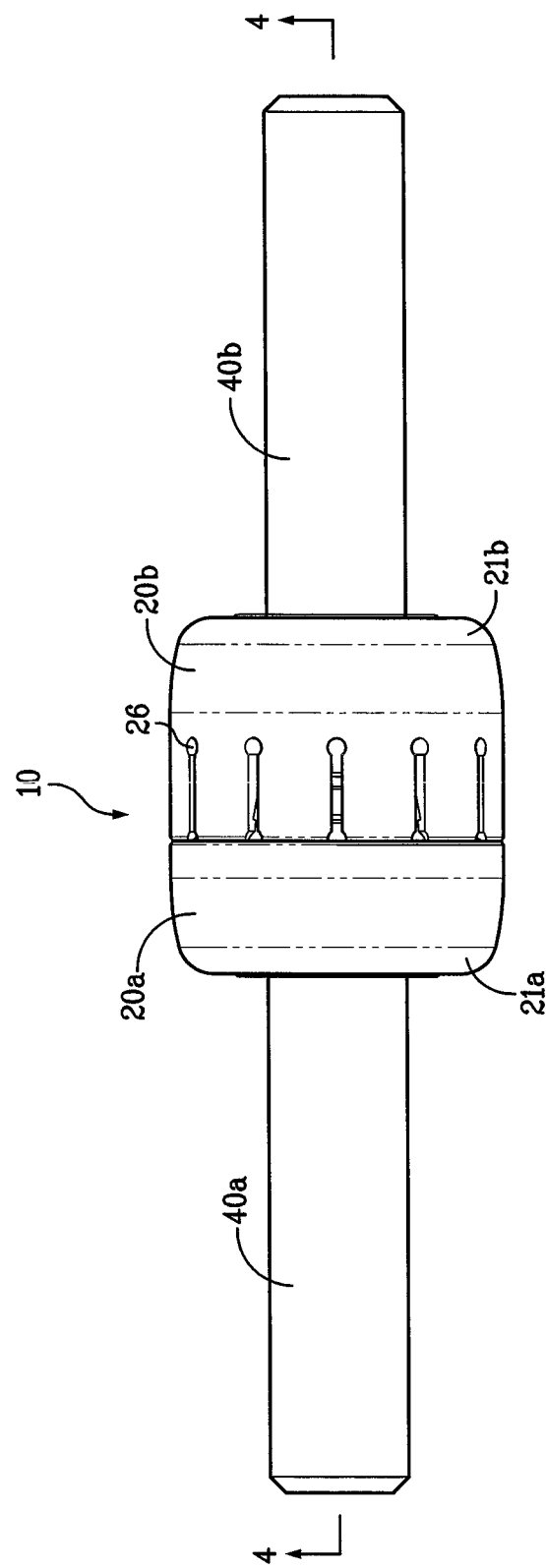
FIG. 3 is a side view of an embodiment of the present invention.
Figure 4:
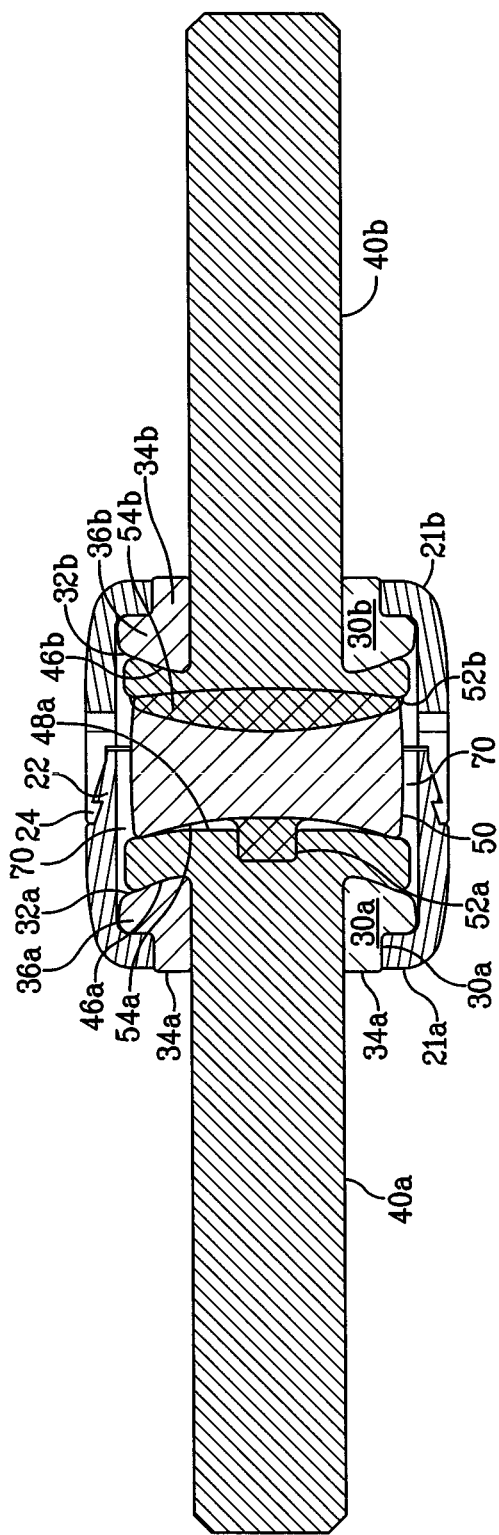
FIG. 4 is a view of an embodiment of the present invention taken along line 4-4 of FIG. 3.

As shown in FIGS. 2 and 4, the central flexible element 50 is situated between the proximal ends of the elongated members 40a, b. The shape of the central element 50 is designed to maximize contact with the proximal ends of the elongated members 40a, b as described in greater detail below, while leaving a space 70 between element 50 and the housing 20 to allow for distortion of the shape of the central flexible element 50 when elongated members 40a, b are moved inward.

The central flexible element 50 can be homogeneous or made as a composite to tailor its performance to the particular loading apparatus 10 experiences when implanted. In one embodiment of the present invention, the central flexible element 50 is constructed from an incompressible elastomer such that as elongated members 40a, b are moved inwards, element 50 experiences transverse strain in response to axial strain. A flexible material having a durometer range of 30-65 on the Shore D scale or 20-95 on the Shore A scale and an elongation at break in the range of 200-600% per ASTM D-638 may be utilized to construct the central flexible element 50. The material utilized preferably is biocompatible and exhibits a consistent dynamic response and resists wear over the millions of loading cycles experience by the apparatus 10 when implanted in the spine. One such material is Polycarbonated Polyurethane or PCU known commercially as Chronoflex. One grade of Chronoflex that has been shown to function with the present invention is Chronoflex C 55D.

Figure 10A:
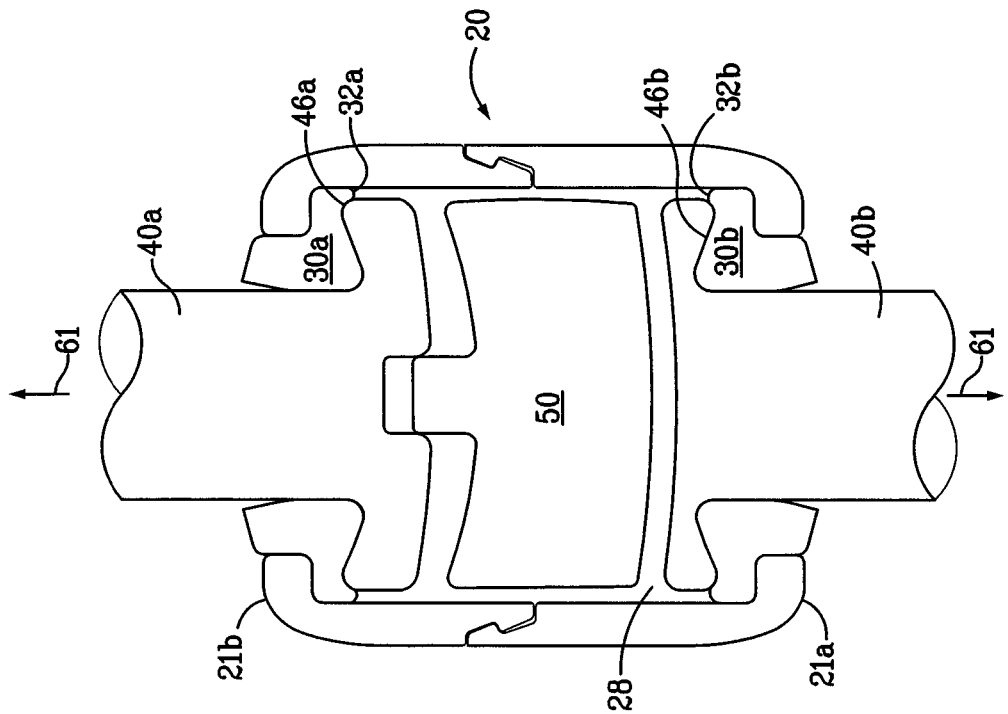
FIG. 10A is a cross section view showing an embodiment of the present invention in an unloaded state.
Figure 11A:
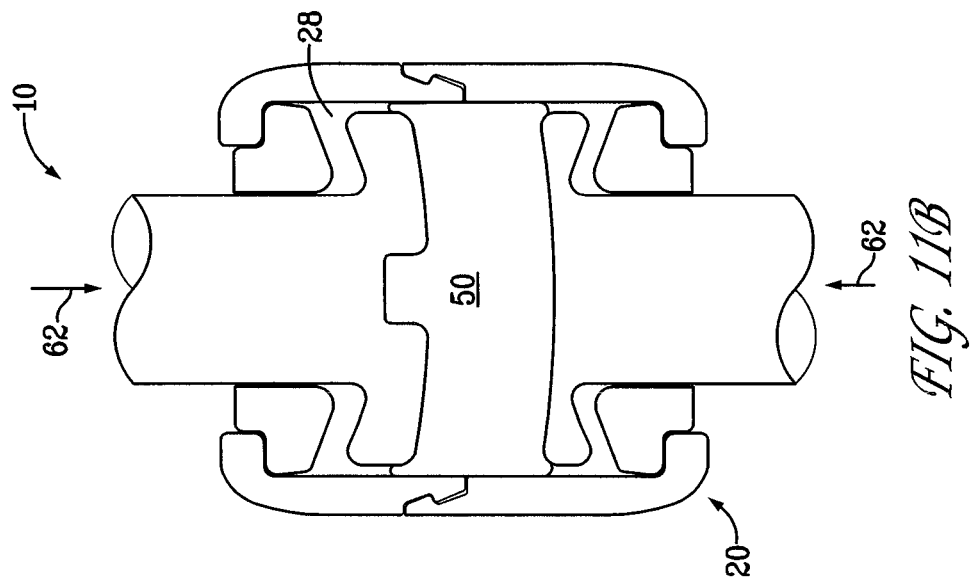
FIG. 11A is a cross section view showing an embodiment of the present invention in compression.

As shown in FIG. 10A the central element is unexpanded when the apparatus 10 is in a neutral, unloaded position. As shown in FIGS. 11A and B, when members 40a, b are moved in the direction of arrows 62, such as would be experience when the spine is extended, element 50 eventually expands into space 70 contacting the inner wall of housing 20. With further movement of the members 40a, b, the element 50 further expands into interstitial space 28. The expansion of the element 50 into spaces 70 and under certain conditions space 28 causes an exponential increase in resistance to compressive loading. This allows for the restricted movement of the adjacent vertebral bodies that apparatus 10 spans while also providing stability thereto.

As shown in FIG. 2, the proximal ends of the elongated arms or members 40a, b are larger than the central and distal portions of the elongated members 40a, b. For example, one or both of the proximal ends comprise flanges 42a, b. The flanges 42a, b include outer surfaces 46a, b facing the distal end of the elongated members 40a, b and inner surfaces 48a, b that face the central element 50. As shown in FIG. 4, the inner surfaces 48a, b of the flanges 42a, b may be convex while the opposing surfaces 54a, b of the central element 50 are concave. Alternatively, the inward surfaces 48a, b may be generally concave while the opposing surfaces 54a, b are convex. In addition, a variety of shapes for the two surfaces may be employed including having both surfaces be flat or having non complimentary geometries. The shape of the surfaces 48a, b and 54a, b will impact the angular and shear displacement between the elongated members 40a, b. The convex and concave shape of surfaces 48a, b and 54a, b respectively act as a rotating joint allowing for articulation as apparatus 10 experiences angular and shear loading.

Figure 5:
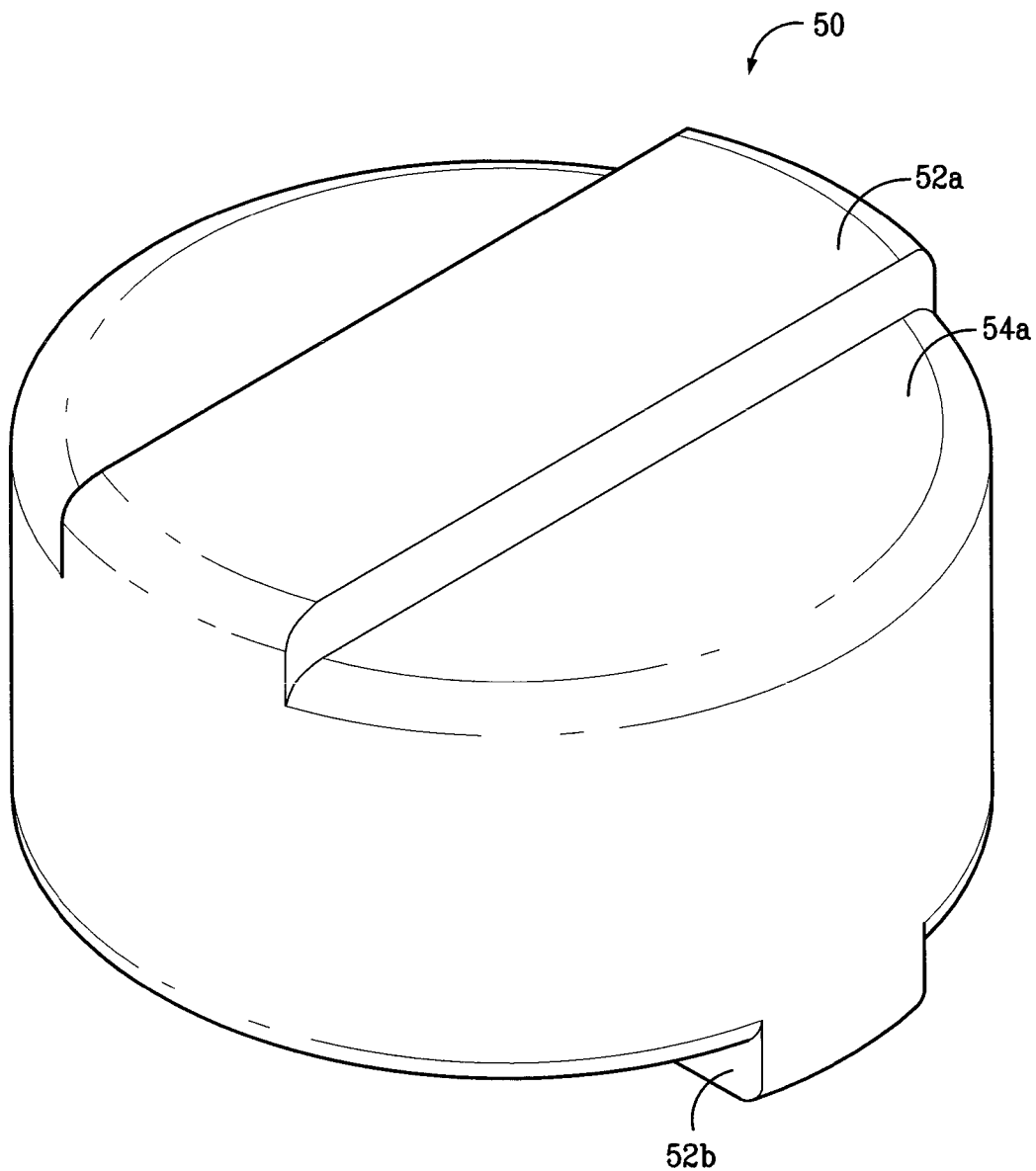
FIG. 5 is an isometric view of an embodiment of the central element of the present invention.

The central flexible element 50 may include one or more features on surfaces 54a, b that allows it to interface with the flanges 42a, b. As shown in FIGS. 2 and 5, the central element 50 includes two ribs 52a, b on the outer surfaces 54a, b. Each flange 42a, b includes a slot 44a, b that corresponds to the geometry of the ribs 52a, b such that the ribs are received and under certain conditions engaged therein. As the elongated members 40a, b are twisted under torsional loading, the ribs 52a, b engage the slots 44a, b acting to resist the twisting movement. The ribs 52 a, b are oriented orthogonally to each other to allow for more consistent performance in angulation and shear. This also allows for implantation of the device without regard to orientation.

Figure 6:
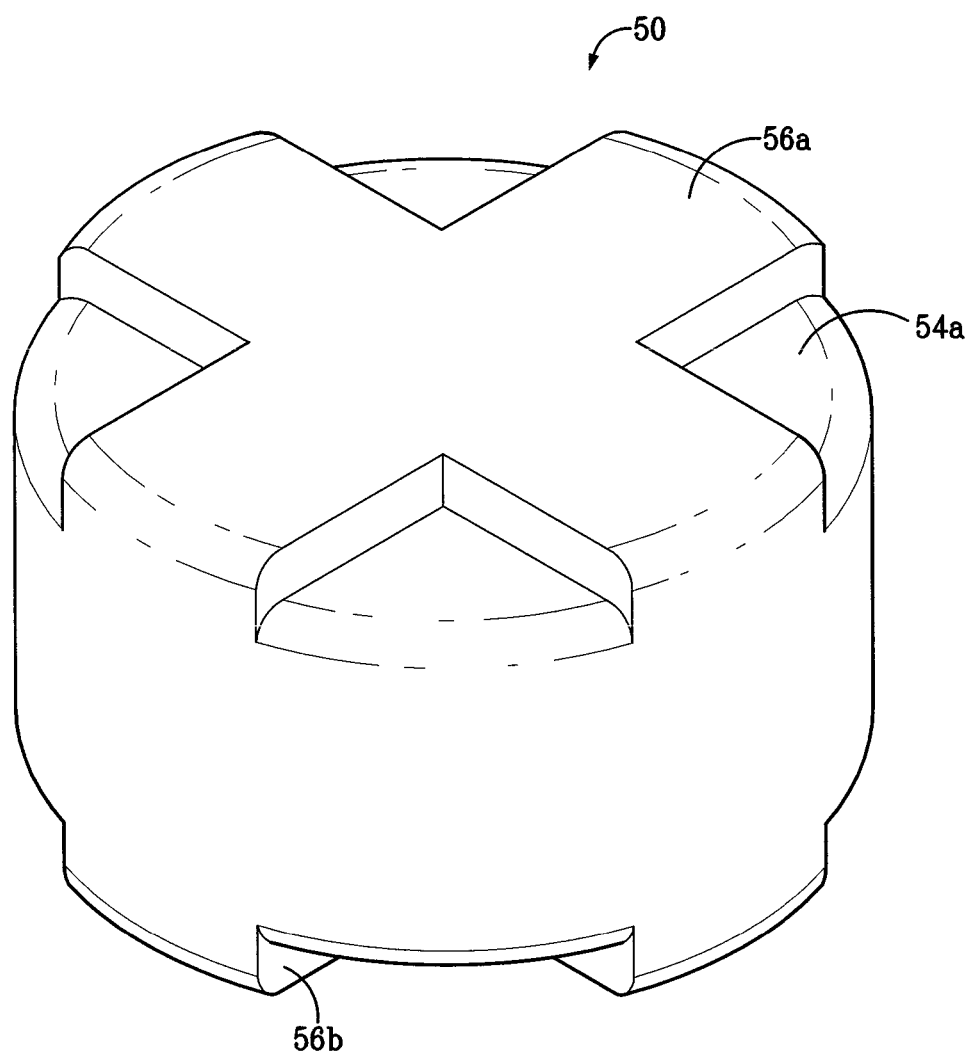
FIG. 6 is an alternative embodiment of the central element of the present invention.
Figure 7:
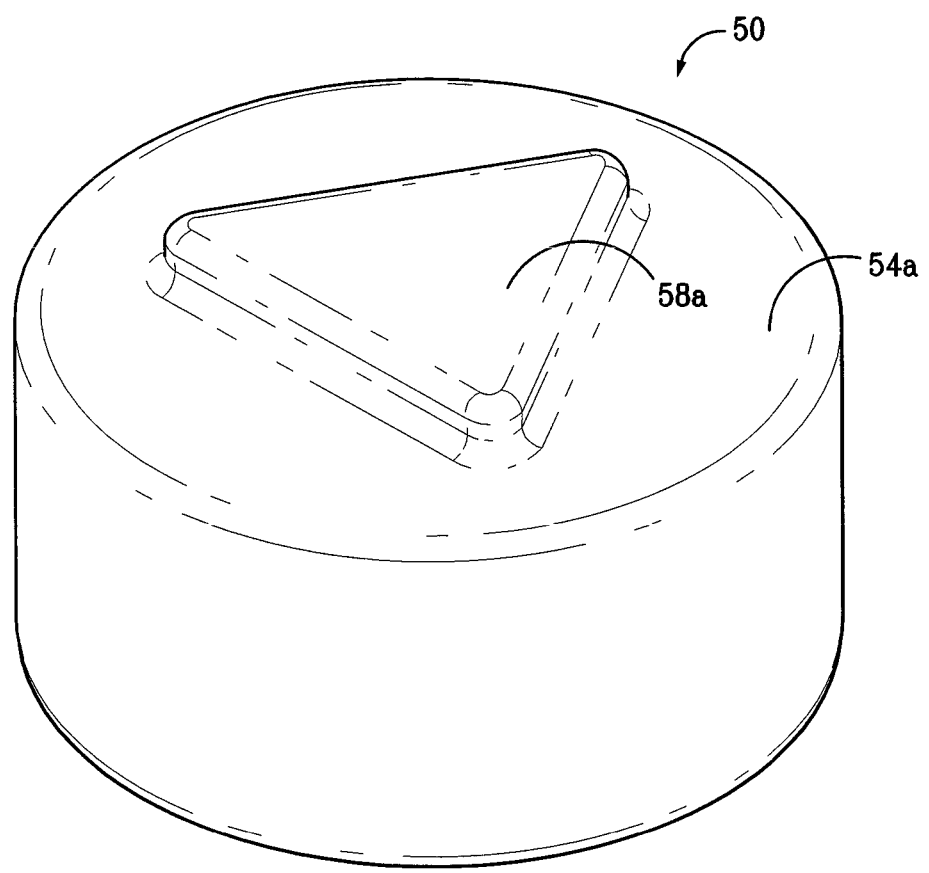
FIG. 7 is an alternative embodiment of the central element of the present invention.
Figure 8:
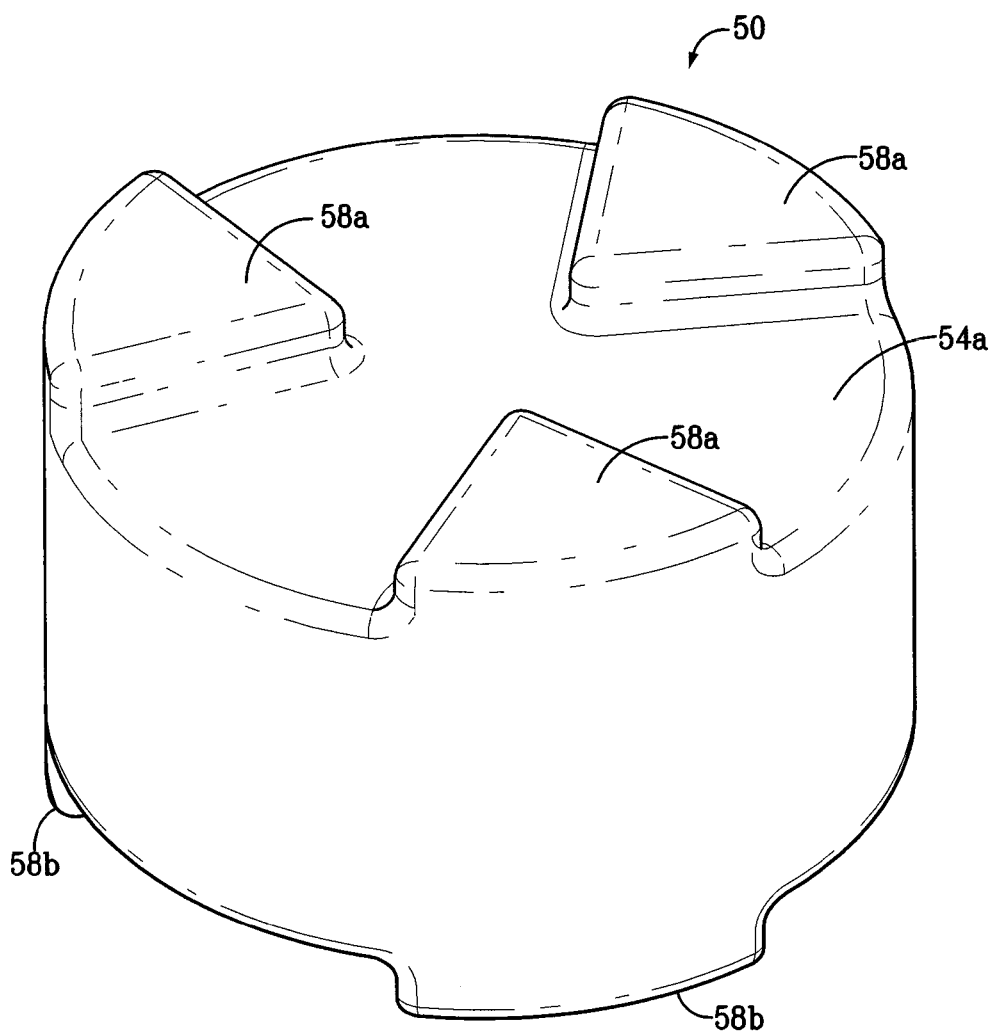
FIG. 8 is an alternative embodiment of the central element of the present invention.

Over time the frictional and compressive forces resulting from the contact between flanges 42a, b and central element 50 will adversely affect the dynamic performance of element 50 due to wear and degredation. Although the central element 50 is constructed from a material that resists wear, the geometry of the features on surfaces 54a, b may be varied in order to increase the durability of the central clement 50. FIGS. 6-9 illustrate examples of geometries that may be employed. FIGS. 2 and 6 shows a plurality of ribs 56a, b disposed on the surface 54a, b such that the amount of surfaces 54a, b that contact the inner surfaces 48a, b are minimized. FIG. 7 shows the central flexible element 50 with centrally located polygons 58 a, b. In addition, the polygons 58 a, b may have any number of sides, for example, forming a star with a plurality of points. As shown in FIG. 8 the central flexible element 50 has a plurality of polygons 58a, b located at the perimeter of central element 50. In this embodiments polygons 58a, b are shown with three sides but could be any number of sides and need not match each other and not be arranged in any pattern.

Figure 9:
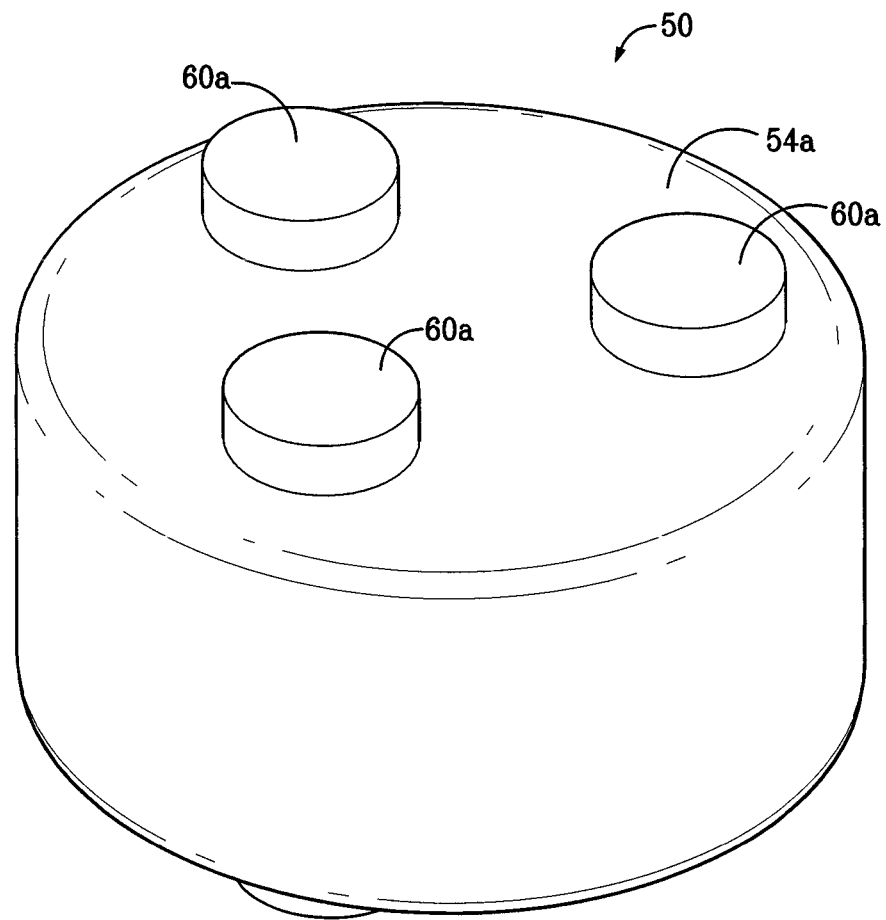
FIG. 9 is an alternative embodiment of the central element of the present invention.

FIG. 9 shows the central flexible element 50 with a plurality of cylindrical protrusions 60a, b positioned in a pattern about the surface 54 a, b of the central flexible element 50. As with the other embodiments, the cylindrical protrusions may be arranged in any manner and need not follow a pattern. In all of the shown embodiments in FIGS. 5-9, the type of engagement features on one side of the central flexible element 50 need not match the engagement features on the opposite side. For example one surface 54a a may have a cruciform 56 a while the other surface 54b has multiple polygons 58 b. In addition, the surfaces 54a, b can each have different types of features such as polygons and cylindrical protrusions thereon.

As shown in FIGS. 2 and 4, a flexible element or elements 30a, b is mounted about the proximal end of one or both of the elongated members 40a, b. The flexible elements 30a, b comprise a collar 34a, b and a central region 36a, b each interacting with housing 20 depending upon the movement of the elongated members 40a, b. For example, the central region 36a, b of the flexible elements 30a, b is acted upon when the elongated members 40a, b are moved in an axial direction. The collar 34a, b may protrude slightly beyond the margin of the housing 20 and is acted upon when the elongated members 40a, b are moved in an angular or radial direction. As with the central flexible element 50 one or both of the flexible elements 30a, b may be constructed form a Newtonian material whereby transverse strain in response to axial strain is described by Poisson's ratio.

Figure 10B:
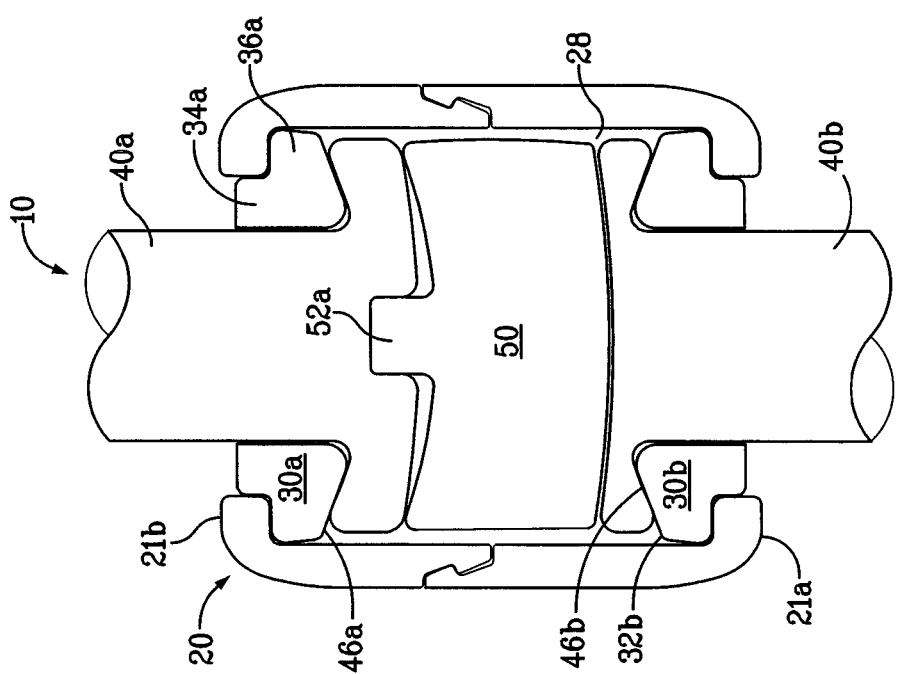
FIG. 10B is a cross section view showing an embodiment of the present invention under tension.

As shown in FIG. 10A an inner surface 32a, b of the central region 36a, b of the collar 34a, b contacts an outer surface 46a, b of the flange 42a, b when the elongated members 40a, b are in a neutral position, for example, when the spine is at rest. Alternatively, a space may exist between the surfaces 32a, b and 46a, b, not shown in the drawings, to allow for greater unrestricted axial movement of elongated members 40a, b. FIG. 10B illustrates the elongated members 40a, b subjected to an axial force causing the members 40a, b to move distally in the direction of arrow 61 such as would be experience when the spine is flexed. The outer surfaces of flanges 46a, b pushes on the flexible members 30a, b at contact surfaces 32 a, b. This in turn causes flexible members 30a, b to come into contact with the housing 20 and deform into interstitial space 28 and/or push the collar 34a, b through an opening in the ends 21a, b of the housing 20. The expansion of the flexible members 30a, b into space 28 and through the ends 21a, b of housing 20 causes an exponential increase in resistance to axial loading. This allows for the restricted and stabilized movement of adjacent vertebral bodies.

A variety of shapes and sizes can be employed for the outer surfaces 46a, b of the flanges 42a, b and the corresponding contacting surface 32a, b of the flexible elements 30a, b. The shape of these surfaces may be varied in order to create a desired dynamic response. Providing a concave shape on surfaces 32a, b may lead to a more rapid deformation of the flexible elements 30a, b and, consequentially more rapid stiffening to limit the range of motion for the elongated members 40a, b. Alternatively, a convex shape may be utilized whereby the flanges 42a, b have a thinner profile allowing for the flexible elements 30a, b to be larger. This may provide for a greater range of motion to the elongated members 40a, b.

As shown in FIGS. 1-4 the housing 20 may be generally cylindrical and has openings at each end 21a, b allowing elongated members 40a, b to pass there through. In one embodiment of the invention, the housing 20 is constructed from a generally rigid material that will not deform under the physiological loading encountered within the spine. The housing 20 may be formed from a first 20a and a second 20b casing wherein each of the casings 20a, 20b have an opening at ends 21a, b. As shown in FIG. 4, casing 20a includes a locking feature 22 that corresponds to a locking feature 24 on casing 20b so as to form a snap lock. Casing 20b also includes a plurality of expansion slots 26 that aid in assembly of the apparatus as will be described below.

As shown in FIG. 2, the apparatus 10 is assembled by aligning the proximal ends of elongated members 40a, b with the central flexible element 50 such that the protrusions 52a, b correspond to slots 44a, b. The flexible elements 30a, b, which have an opening in the center corresponding to the cross sectional geometry of elongated members 40a, b, are then inserted over the distal ends of elongated members 40a, b and slid into place about the proximal end thereof or in proximity to flanges 42a, b. Thereafter, the distal ends of elongated members 40a, b are placed through the openings in the ends 21a, b of casings 20a, b. The openings in the ends 21 a, b are larger than the cross sectional geometry of the elongated members 40a, b creating a space between the elongated members 40a, b and the housing 20. Casings 20a, b are placed together and inward pressure applied thereon such that locking features 22 slides under locking feature 24 which moves in a radial direction as facilitated by expansion slots 26 locking casings 20a, b together. The casings can also be assembled by welding, bolting, threading, screwing, adhesive bonding, magnetic coupling, clamping, or twist locking. Once casing 20 is assembled, the proximal ends of members 40a, b, the central element 50, the flexible elements 30a, b and the flanges 42a,b are contained therein. The collars 34a, b of flexible elements 30a, b, however, are located in the spaces between the housing 20 and members 40a, b and may slightly protrude through the space between the elongated members 40a, b and the openings at the ends 21a, b of the housing 20.

FIG. 12 illustrates the apparatus 10 implanted in the spine between adjacent vertebral bodies 8a, b in order to provide stability to the joint existing between vertebrae 8a, b. Typically, stabilization devices such as apparatus 10 are mounted to the vertebral bodies 8a, b via an anchoring device 3. Once mounted to the spine 2 the apparatus 10 serves to stabilize adjacent vertebral bodies while also allowing for motion.

Figure 11B:
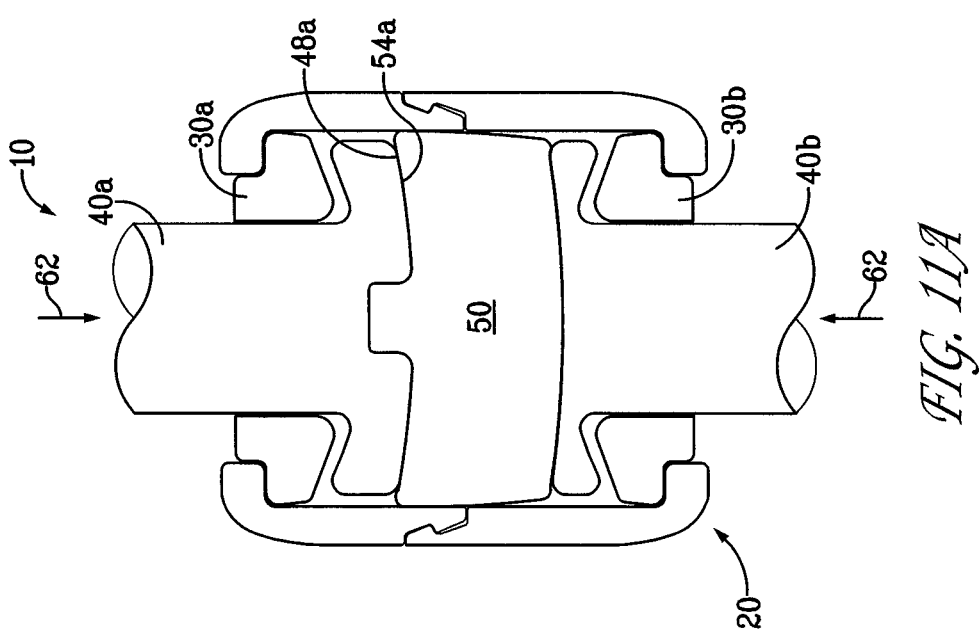
FIG. 11B is a cross section view showing an embodiment of the present invention in a further compressed state.
Figure 14:
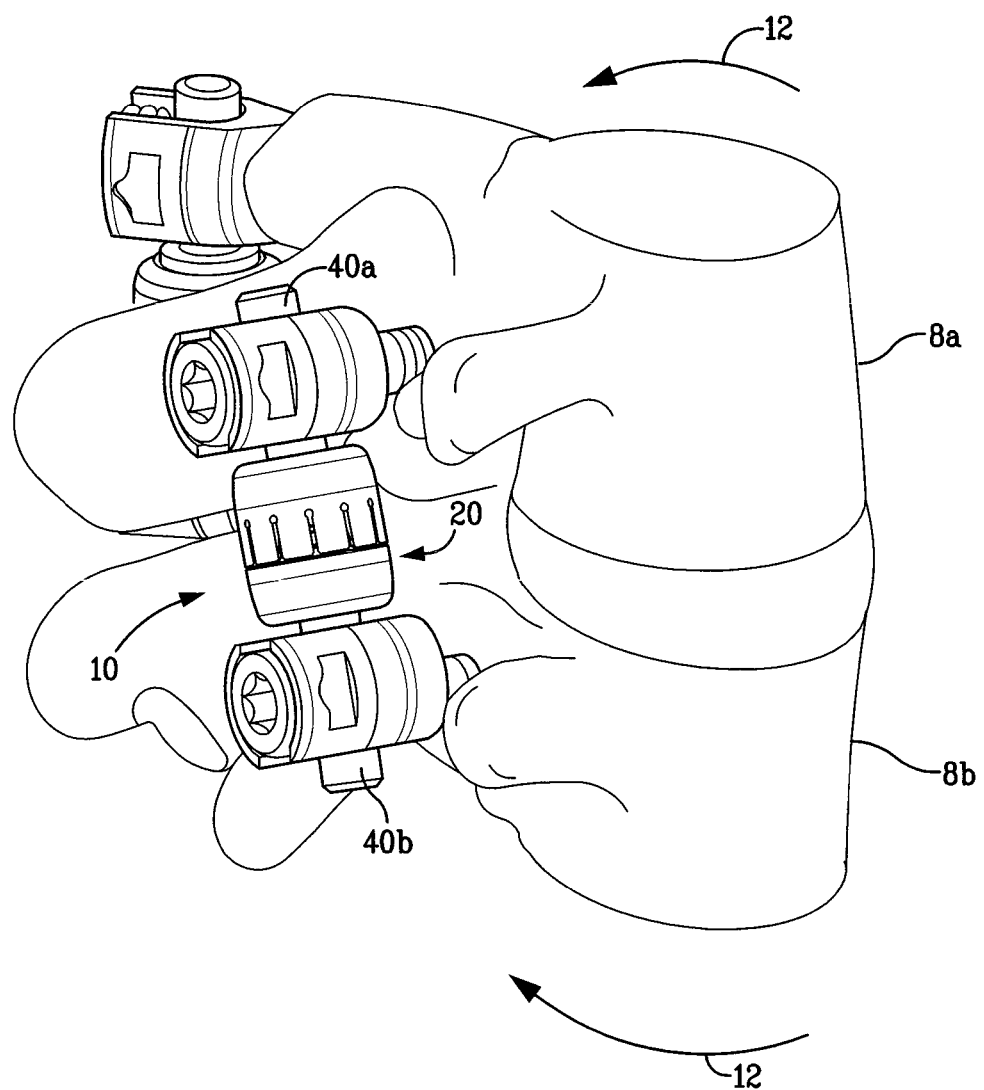
FIG. 14 is a side view showing an embodiment of the present invention placed on a section of the spine whereby the section of the spine is in extension.
Figure 15:
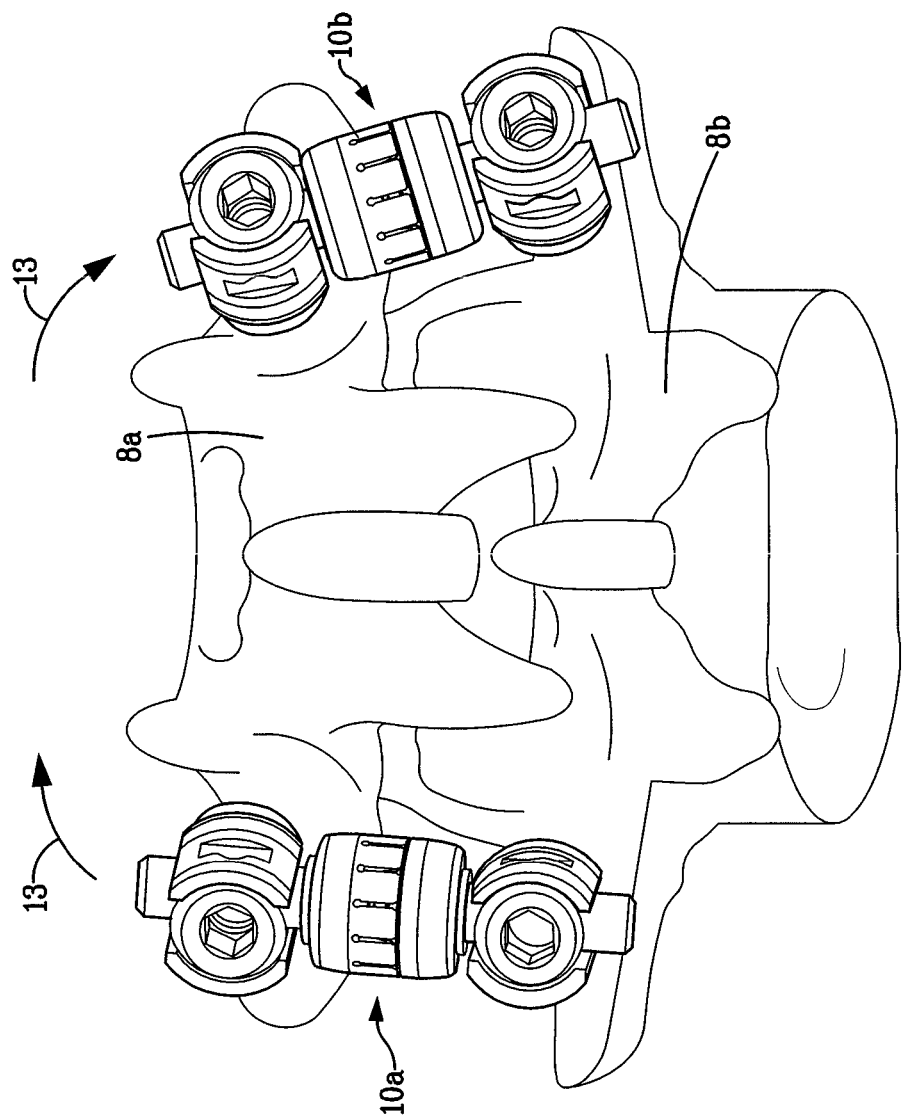
FIG. 15 is a posterior view showing an embodiment of the present invention placed on a section of the spine whereby the section of the spine experiences lateral bending.

As shown in FIGS. 10A-B, when the spine 2 is moved in the direction of arrows 11 the elongated members 40a, b transfer force to the flexible elements 30a,b as described above allowing for a limited range of motion. As shown in FIGS. 11A-B and 14 when the spine is moved in the direction of arrows 12 or placed in extension the elongated members 40a, b moved toward the central flexible element 50. The central flexible element 50 expands into spaces 70 and under certain conditions, for example increased extension of the spine creating the dynamic response discussed above. As shown in FIG. 15, the spine 2 is experiencing lateral or side bending, as indicated by the arrows 13. Under the lateral loading shown in FIG. 15 apparatus 10a will transfer the loading forces to flexible members 30a, b while the apparatus 10b will transfer loading to the central flexible element 50.

Figure 16:
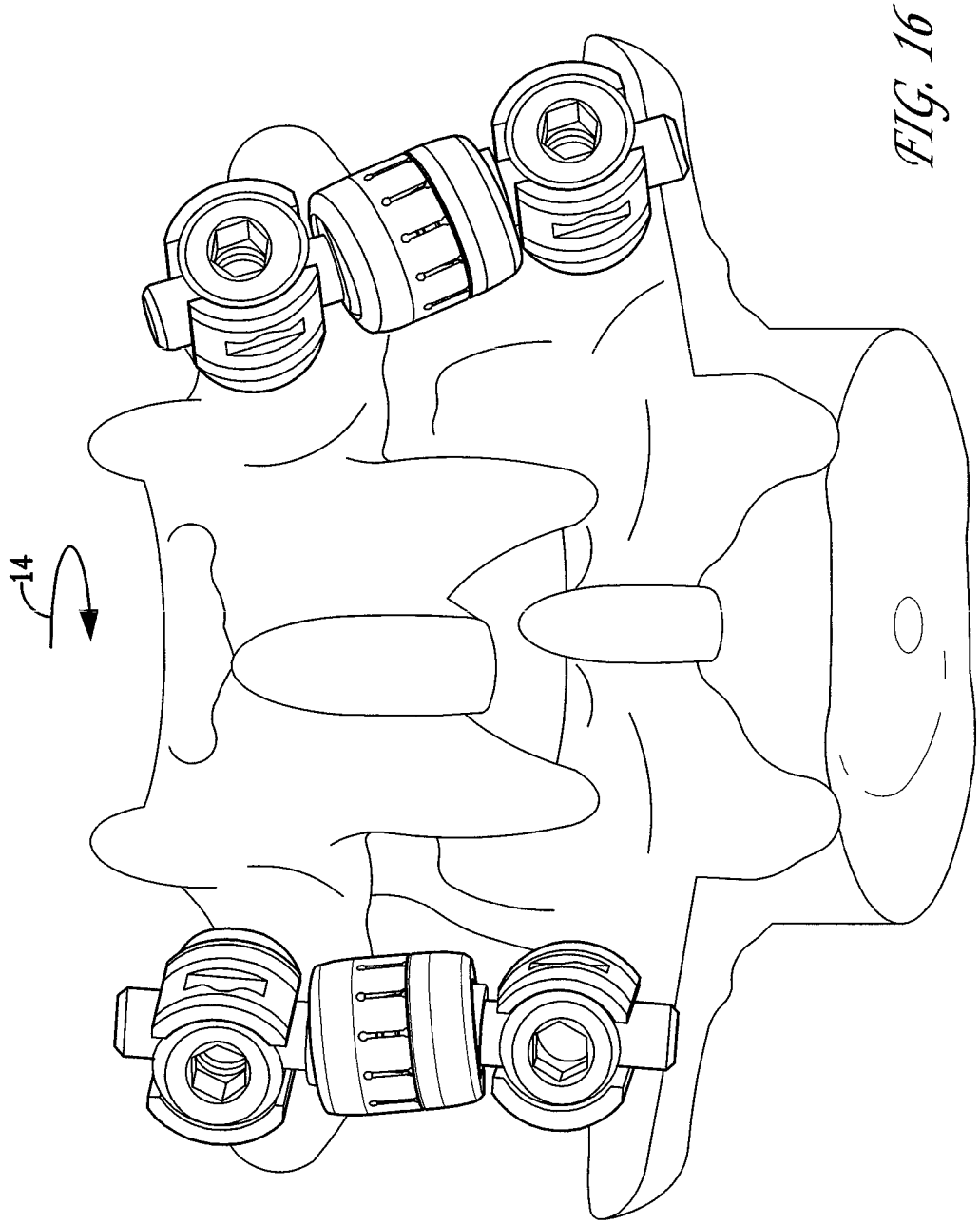
FIG. 16 is a posterior view showing an embodiment of the present invention placed on a section of the spine whereby the section of the spine experiences axial rotation.
Figure 17:
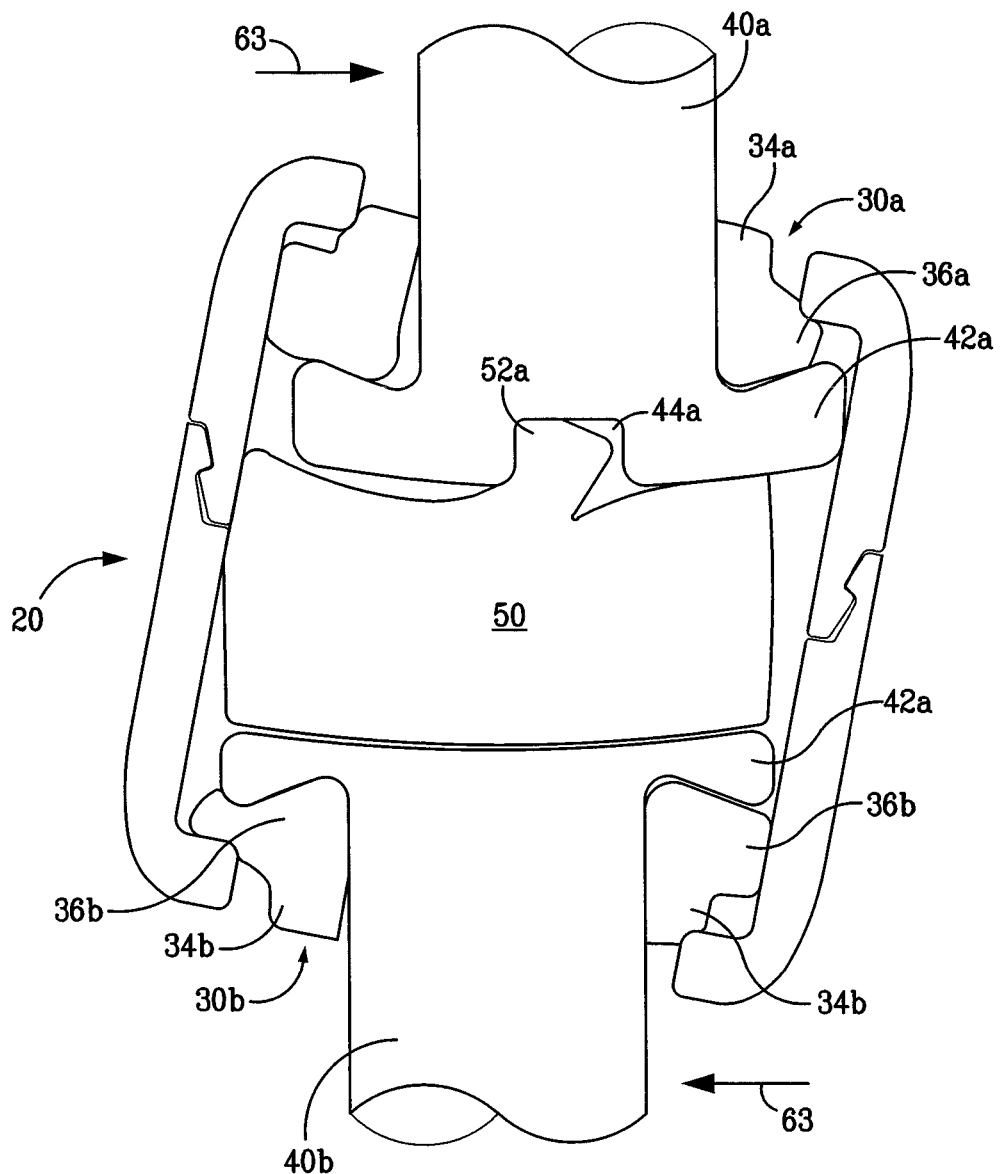
FIG. 17 is a cross section view showing an embodiment of the present invention actuated under shear.

FIG. 16 shows the spine rotated about its axis in the direction of arrow 14. Due to the apparatus 10 being mounted away from the axis of the spine the device 10 experiences shear loading. As shown in FIG. 17 the elongated members 40a, b are moved in the direction indicated by arrows 63. As the elongated members 40a, b are moved, surfaces 48a, b and 54a, b shift relative to each other such that flange 42a, b is free to interact with additional flexible elements 30a, b. As the flanges 42a, b contact additional flexible elements 30a, b, they impinge upon the housing 20. Thereafter, the additional flexible elements 30a, b resist movement in the manner described above with reference to the distal movement of the elongated members 40a, b. This dynamic response maintains the elongated members 40a, b roughly parallel to each other as the central flexible element 50 and the housing 20 rotate.

Figure 13:
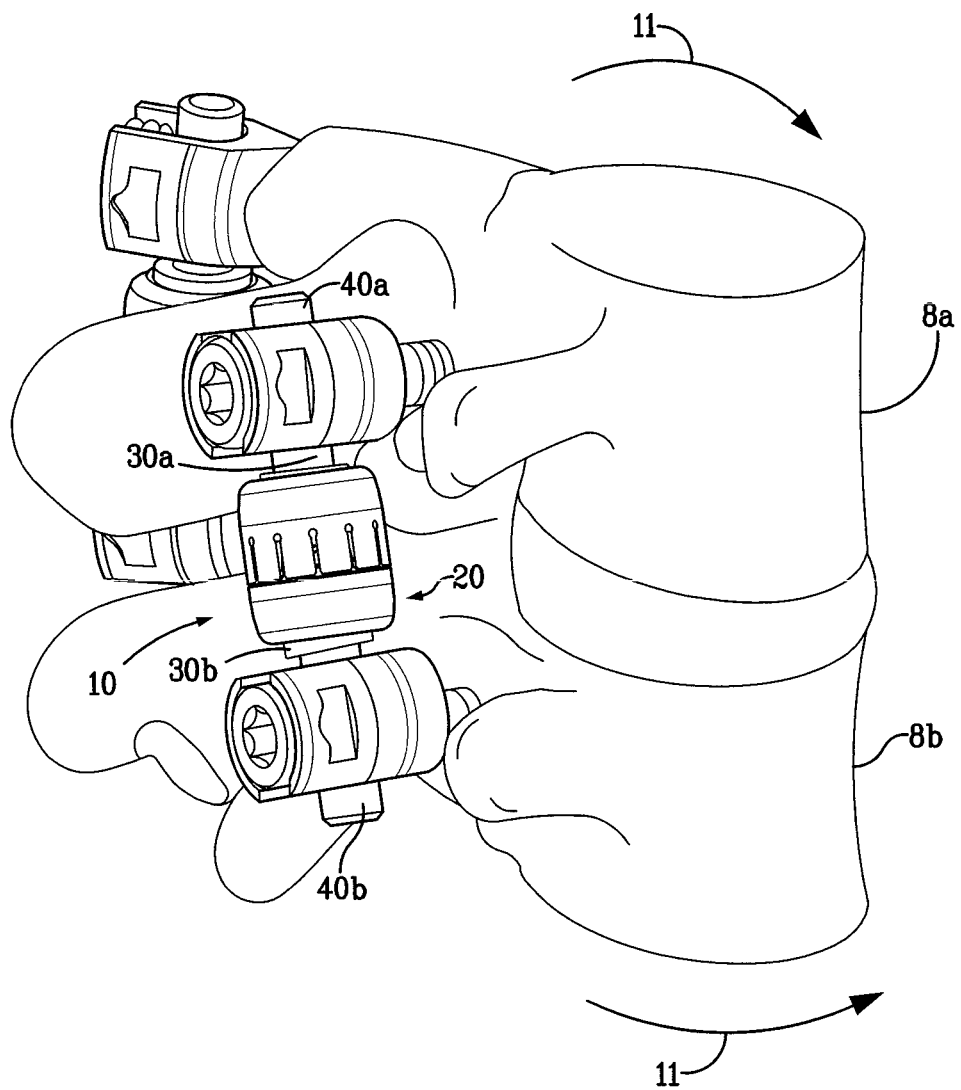
FIG. 13 is a side view showing an embodiment of the present invention placed on a section of the spine whereby the section of the spine is in flexion.
Figure 18:
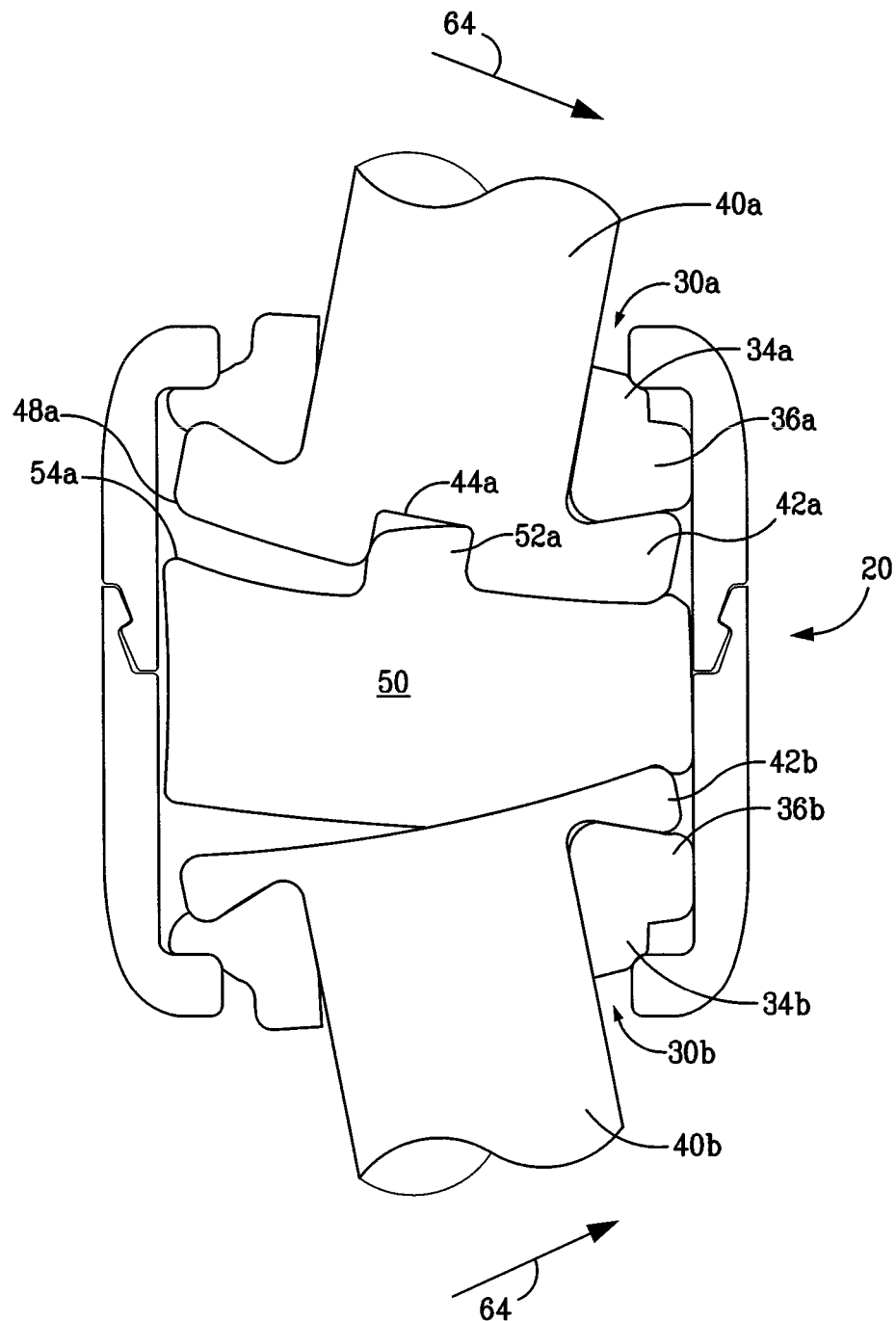
FIG. 18 is a cross section view showing an embodiment of the present invention angulated.

Apparatus 10 has been described above primarily with reference to unidirectional loading conditions. As shown in FIG. 18, however, the apparatus 10 can handle loading in multiple directions simultaneously. For example, as shown in FIG. 13 the elongated members 40a, b are moved both distally and obliquely from each other causing the additional flexible elements 30a, b interact with the flanges 42a, b and the housing 20 in a manner as described above. The space between the housing 20 and the elongated members 40a, b into which collars 34a, b are placed allows elongated members 40a, b a range of angular motion that is restricted in the direction of movement by the additional flexible elements 30a, b whereby collars 34a, b act as a buffer between the housing 20 and the elongated members 40a, b.

Although the present invention has been described above with respect to particular preferred embodiments, it will be apparent to those skilled in the art that numerous modifications and variations can be made to these designs without departing from the spirit or essential attributes of the present invention. Accordingly, reference should be made to the appended claims, rather than to the foregoing specification, as indicating the scope of the invention. The descriptions provided are for illustrative purposes and are not intended to limit the invention nor are they intended in any way to restrict the scope, field of use or constitute any manifest words of exclusion.

What is claimed:

1. An apparatus comprising:
   at least two elongated members having a distal and proximal end, the proximal end comprising a flange, wherein the flange comprises a proximal surface and a distal surface;
   a first flexible element disposed between the proximal ends of the at least two elongated members, wherein the first flexible member has a first and a second outward facing surface and further wherein the proximal surface of each of the flanges interacts with at least one of the outward facing surfaces of the first flexible element to form an anti-torsional coupling;
   first and second additional flexible elements, each additional flexible element having a collar at least partially surrounding the proximal end of a corresponding elongated member; and
   a housing having a first and a second end encapsulating the proximal ends of said members such that the first flexible element and the first and second additional flexible elements are contained therein wherein the first collar protrudes through an opening in the first end of the housing.

2. The apparatus of claim 1 wherein the anti-torsional coupling further comprises at least one protrusion on each of the outer facing surfaces of the first flexible element and at least one corresponding recess on the proximal surface of each of the flanges that receives said at least one protrusion.

3. The apparatus of claim 2 wherein the at least one protrusion on a first of the outward facing surfaces of the first flexible element is oriented so as to be offset from the at least one protrusion on a second of the outward facing surfaces of the first flexible element at a pre-determined angle.

4. The apparatus of claim 2 wherein the at least one protrusion comprises a rib that transverses the outward facing surface.

5. The apparatus of claim 2 wherein the at least one protrusion comprises at least two transverse ribs that intersect.

6. The apparatus of claim 2 wherein the at least one protrusion comprises at least one polygon.

7. The apparatus of claim 1 wherein the proximal surface is generally convex and contacts a surface of the first flexible element.

8. The apparatus of claim 1 wherein the distal surface is generally concave and contacts a surface of the at least one additional flexible element.

9. The apparatus of claim 1 wherein the anti-torsional coupling further comprises at least one recess on each of the outer facing surfaces of the first flexible element and at least one corresponding protrusion on the inward surface of each of the flanges that receives said at least one recess.

10. The apparatus of claim 1 wherein the housing, the first flexible element and the first and second additional flexible elements cooperate to define a space to permit deformation of the first flexible element in a lateral direction.

11. A stabilization apparatus for implantation into a spine comprising:
    a first and a second elongated member each having a distal and proximal end;
    an enlarged region located at the proximal end of each elongated member, each enlarged region having a proximal and a distal face;
    a first flexible element disposed between the enlarged regions of each elongated member, wherein the first flexible member has a first and a second outward facing surface and further wherein the proximal face of each of the enlarged regions interacts with at least one of the outward facing surfaces of the first flexible element to form an anti-torsional coupling;
    a first and second additional flexible element at least partially surrounding the proximal end of a corresponding elongated member in proximity with the enlarged regions, wherein the first and second additional elements further comprise a collar; and
    a housing encapsulating the first flexible element, the enlarged regions, and the additional flexible elements wherein the first flexible element and additional flexible elements interact with the enlarged regions and the housing to permit movement of the elongated members in a direction complimentary to the movement of the spine, wherein the collar of the first additional flexible element protrudes through an opening in a first end of the housing.

* * * * *